(12) United States Patent
Collins

(10) Patent No.: US 6,702,785 B1
(45) Date of Patent: Mar. 9, 2004

(54) NEEDLE CAPPER

(76) Inventor: Sonya Dené Collins, 136-A Northampton St., Boston, MA (US) 02118

( * ) Notice: Subject to any disclaimer, the term of this patent is extended or adjusted under 35 U.S.C. 154(b) by 0 days.

(21) Appl. No.: 09/455,390

(22) Filed: May 4, 2000

(51) Int. Cl.$^7$ ............................................... A61M 5/32
(52) U.S. Cl. ........................ 604/192; 604/197; 604/198
(58) Field of Search ................................ 604/110, 192, 604/197, 198, 263

(56) References Cited

U.S. PATENT DOCUMENTS

| | | | | |
|---|---|---|---|---|
| 4,318,403 A | * | 3/1982 | Sneider | 604/2 |
| 4,775,369 A | * | 10/1988 | Schwartz | 604/263 |
| 4,850,976 A | * | 7/1989 | Heinrich et al. | 604/192 |
| 5,139,489 A | * | 8/1992 | Hollister | 604/192 |
| 5,232,454 A | * | 8/1993 | Hollister | 604/192 |
| 5,232,455 A | * | 8/1993 | Hollister | 604/192 |
| 5,368,580 A | * | 11/1994 | Suzuki | 604/263 |
| 5,472,433 A | * | 12/1995 | Suzuki | 604/263 |
| 5,498,243 A | * | 3/1996 | Vallelunga et al. | 604/197 |
| 5,858,008 A | * | 1/1999 | Capaccio | 604/263 |
| 6,102,893 A | * | 8/2000 | Aneas | 604/110 |

* cited by examiner

*Primary Examiner*—Brian L. Casler
*Assistant Examiner*—Jeremy Thissell

(57) ABSTRACT

The Needle Capper is a single-cased 4 unit which houses used syringes 9/hypodermic needles 10. The Needle Capper is comprised of two plastic half-tubes 4 fitting around the syringe 9/hypodermic needle 10, hinged together at the bottom ends. A rubber cork 2 is located at the top of the hinge. The tip of the used needle 10 is inserted or depressed into the cork 2, causing the hinge of the two halves to raise and join together, thereby closing the case 4. When the case is closed, the connector button clasps male 6 and female 7, located on the handles join. The user then snaps the handles together, thereby locking the case. The needle is sealed inside the case and ready for proper disposal.

4 Claims, 2 Drawing Sheets

NEEDLE CAPPER

FIELD OF INVENTION

Needle Capper is a case designed for the safe disposal of hypodermic needles and syringes using the one hand method. Needle Capper is designed to be used in the operating room and physicians' offices for disposal/transport of used needles, as well as in the home by diabetics.

BACKGROUND OF INVENTION

HEALTH CARE INDUSTRY

"Expenditures on health care in the United States are expected to rise by more than 12% in 1994 to exceed one trillion dollars for the first time. Continued growth is the envisioned for home health care as well as managed care organizations for the balance of the decade. The reduction of consistent double-digit rates of increase in health care expenditures will require a sustained national commitment and accommodation by health care providers and consumers." (U.S. Industrial Outlook)

In 1993, there were two million nurses and six hundred fifty thousand doctors employed in the health are field. The following chart high lights the various medical facilities:

| FACILITY | NUMBER |
| --- | --- |
| Medical Schools | 126 |
| Hospitals | 6600 |
| Health Insurance Companies | 1100 |
| Nursing Care Facilities | 25600 |

The health care field employment sector is leading the way in the economy form 9.1. million workers in Jun. 1990 to 10.2 million in June 1993. Home health care facilities and workers are in the fastest growing segment of the health care industry, where employment increased to 473,100 in June 1993 from 290,900 in June 1990. According to recent statistics, U.S. health care rose by approximately 12 percent to 942.5 billion dollars in 1993; this represents about thirty-nine hundred dollars per capita.

The U.S. Medical and Dental Instruments and Supplies segment of the economy, with its value estimated at 34.9 billion dollars, represents five specific sectors: Medical Supplies (13.2 billion dollars), X-ray Apparatus (3.1 billion dollars), Electromedical (5.8 billion dollars) Medical Instruments (11.1 billion dollars) and Dental Equipment (1.8 billion dollars)

"The value of shipments by the U.S. medical equipment and supplies industry rose more than 8 percent in 1993. This increase was partly due to the strong overseas demand for U.S. medical equipment. Industry employment increased to an estimated two hundred eighty-seven thousand. Among the major medical product groupings, the surgical appliances and supplies segment, which accounted for thirty-eight percent of the total medical equipment shipments, experienced another year of strong growth, at a rate of nearly ten percent in constant dollars, reaching 13.2 billion dollars in 1993. Manufacturers of surgical and medical instruments also experienced solid growth, as shipments increased nearly seven percent to eleven billion dollars." (U.S. Industrial Outlook)

According to the Universal Health Care Almanac, the number of all surgical operations was 23.8 million in 1993. The total of outpatient emergency visits in 1993 was 97.3 million.

OUTLOOK: HEALTH CARE

Health care costs continue to rise for a number of reasons including expensive technologies, increasing number of accidents and crimes, and duplication of unnecessary tests, based on recent information. As a result, this segment of the economy is termed the largest. The government, insurance companies and patients alike are awaiting remedies to decrease per capita health care costs.

DIABETES

According to the American Diabetes Association (ADA), more than sixteen million Americans have diabetes. The ADA also reports that every minute another person is diagnosed with diabetes. It is the nation's fourth-leading cause of death by disease, accounting for over one hundred sixty-two thousand diabetes-related deaths in 1996. It is also the leading cause of kidney failure, non-traumatic amputations, heart disease, stroke and blindness. The disease, for which there is no know cure, cost the U.S. 138 billion dollars every year.

Worldwide, the numbers of diabetes patients is estimated at one hundred thirty-five million, according the International Diabetes Federation. The number of cases has tripled since 1985 and is set to rise to 300 million by 2025. Developing countries will bear the brunt of this acceleration with a two hundred percent rise. The dramatic rise is mainly attributed to the increased in the cases of non-insulin-dependent (NIDDM) or type 2 diabetes which is linked to population aging and unhealthy lifestyles. Recent statistics reveal that in 1996 in the U.S., AIDS and Cancer deaths have been successfully reduced while diabetes deaths continue to increase by two to three percent.

OUTLOOK: DIABETES

Diabetes is a disease that affects 135 million people worldwide, and is projected to affect 300 million by 2025.

The vast number of people who suffer from the condition create a large market for products that make life and living easier for them.

SUMMARY OF THE INVENTION

Needle Capper addresses the need for safe, sanitary disposal/transport of used hypodermic needles and syringes. Individual cases grip and lock in the needles that may carry disease-causing viruses. It protects health professional, waste management workers, and other people who deal with such hazards regularly. Once a needle is encased in Needle Capper, accidental pricks with a used needle are virtually impossible. Not only does it reduce the risk of infection cased by handling contaminated needles, but its protection offers peace of mind to the individuals the device serves. Diabetics as well will appreciate Needle Capper as a responsible way to dispose of needles and protect others.

DETAILED DESCRIPTION

Figure 1:
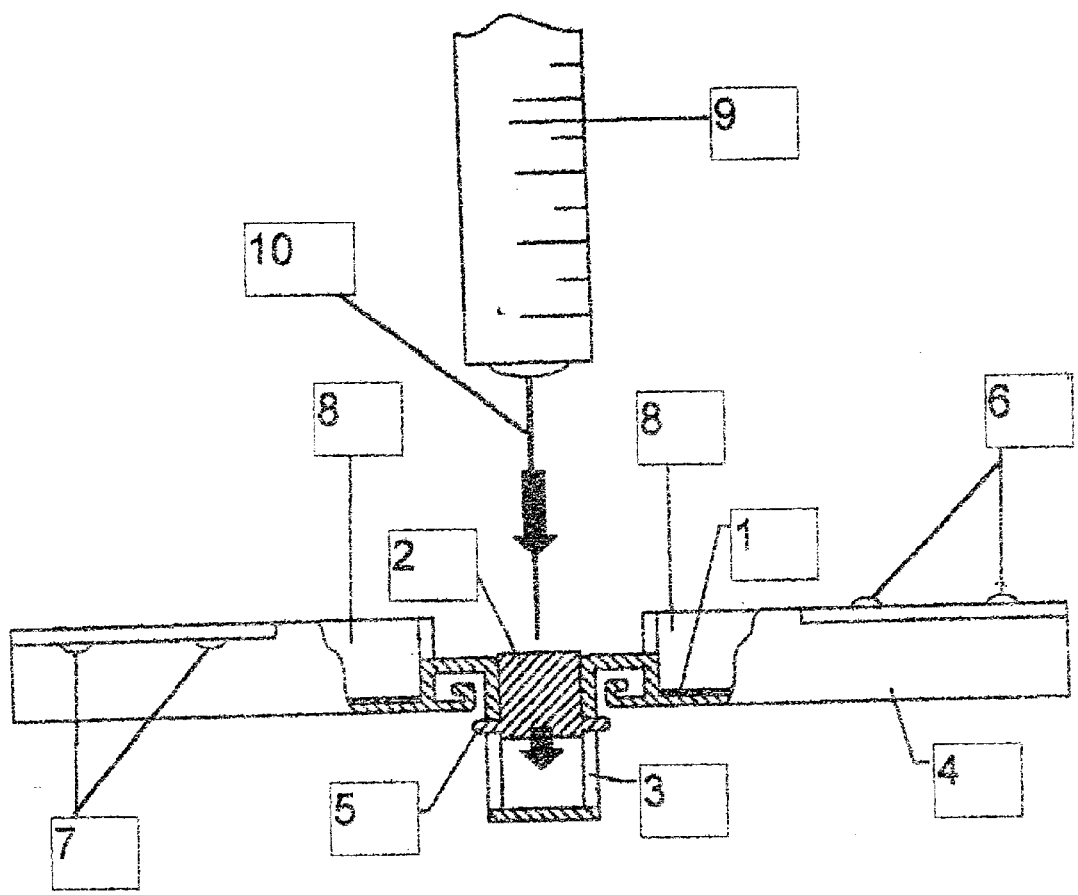
FIG. 1 is a view of the instant invention before use, with wings open.
Figure 2:
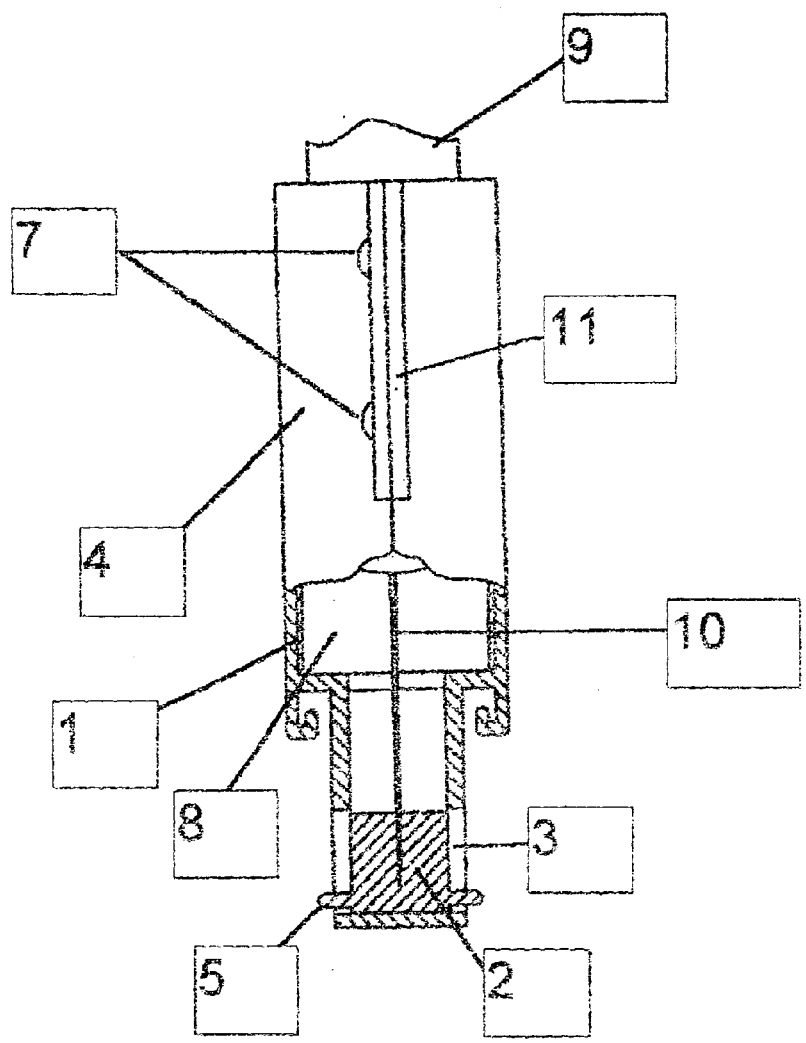
FIG. 2 is the same view of the instant invention but with wings closed.

Needle Capper comprises two plastic half-tubes 4 that fit around a syringe, hinged together at the bottom ends. A rubber or Styrofoam cork 2 is located on top of the hinge 3.

Using the one hand method the tip of the used needle 10 is inserted into the cork 2; when depressed, the hinge 3 raises the two halves 4 of the case, joining them, and thereby closing the case. Two handles, with male and female clasps 7 of opposing handles are able to be locked together. The user snaps the handles together, thereby locking the case. The needle 10 and syringe 9 are sealed inside the case 4, ready for disposal.

What is claimed is:

1. A needle protection device for the safe disposal of syringes having projecting needles, the needle protection device comprising:

a stopper for receiving the needle to cover the point of the needle;

a track for slidably mounting the stopper, the track having a base abutable by the stopper when the stopper slides in the track as the needle is urged thereagainst by axial movement of the syringe;

at least a pair of shells pivotally attached to the track for movement from an open position where the shells extend laterally with respect to the axes of the needle and syringe to a closed position where the shells extend in the direction of the axes of the needle and syringe and enclose the syringe in a housing while at least the point of the needle is covered by the stopper.

2. The needle protection device of claim 1 wherein the stopper is made of a material penetratable by the needle so that the point of the needle becomes embedded therein.

3. The needle protection device of claim 2 wherein the shells have cooperating latch members which engage and lock closed the housing formed by the shells.

4. The needle protection device of claim 3 wherein the shells have a stiff plastic outer layer and a cushioned inner layer, and wherein the track is made of stiff plastic, the hinges being provided by relieved portions in the plastic.

\* \* \* \* \*